(12) United States Patent
Kimmig (10) Patent No.: US 10,996,355 B2
(45) Date of Patent: May 4, 2021

(54) METHOD AND ARRANGEMENT FOR DETECTOR CORRECTION FOR GENERATING OBJECT RADIOGRAPHS

(71) Applicant: Carl Zeiss Industrielle Messtechnik GmbH, Oberkochen (DE)

(72) Inventor: Wolfgang Kimmig, Aalen (DE)

(73) Assignee: Carl Zeiss Industrielle Messtechnik GmbH, Oberkochen (DE)

( * ) Notice: Subject to any disclaimer, the term of this patent is extended or adjusted under 35 U.S.C. 154(b) by 294 days.

(21) Appl. No.: 16/258,300

(22) Filed: Jan. 25, 2019

(65) Prior Publication Data

US 2019/0235100 A1    Aug. 1, 2019

(30) Foreign Application Priority Data

Jan. 26, 2018    (DE) .................... 10 2018 201 249.0

(51) Int. Cl.
*A61B 6/00*    (2006.01)
*G01T 7/00*    (2006.01)
(Continued)

(52) U.S. Cl.
CPC .......... *G01T 7/005* (2013.01); *A61B 6/4225* (2013.01); *A61B 6/4233* (2013.01); *A61B 6/585* (2013.01);
(Continued)

(58) Field of Classification Search
CPC ....... A61B 6/032; A61B 6/5258; A61B 6/583; A61B 6/4085; A61B 6/4291; A61B 6/5282; A61B 6/585; G01N 2223/419;
(Continued)

(56) References Cited

U.S. PATENT DOCUMENTS 5,774,519 A    6/1998  Lindstorm et al.
6,047,039 A    4/2000  Flohr
(Continued)

FOREIGN PATENT DOCUMENTS

DE        19835451 B4    3/2005
DE     102004044698 A1   3/2006
(Continued)

OTHER PUBLICATIONS

Boas at al, "CT artifacts: causes and reduction techniques" , In: Imaging in Medicine 4 (2), 2012, 229-240, (2012).
(Continued)

*Primary Examiner* — Dani Fox
(74) *Attorney, Agent, or Firm* — Falk Ewers; Ewers IP Law PLLC (57) ABSTRACT

A method for correcting a detector configured to generate object radiographs and an arrangement to implement the method is provided. The method includes the steps of (a) providing the detector having setting values for a gain and offset correction, (b) capturing a plurality of object radiographs of a test object by the detector and generating a reconstructed three-dimensional representation of the test object based on of the object radiographs, (c) determining at least one quality value of the reconstructed three-dimensional representation, repeating the steps (b) and (c) at least once, wherein before the repetition, a parameter set is generated and a measurement sequence is implemented on the basis thereof, at least one setting value for a gain and offset correction of the detector being determined anew based on the measurement sequence; and (e) determining a preferred gain and offset correction based on overall determined quality values.

12 Claims, 6 Drawing Sheets

(51) Int. Cl.
  *H04N 5/365* (2011.01)
  *G01N 23/04* (2018.01)
  *G01T 1/16* (2006.01)
  *G03B 42/02* (2021.01)
  *H04N 5/32* (2006.01)

(52) U.S. Cl.
  CPC .............. *G01N 23/04* (2013.01); *G01T 1/16* (2013.01); *G03B 42/02* (2013.01); *H04N 5/32* (2013.01); *H04N 5/3658* (2013.01)

(58) Field of Classification Search
  CPC .......... G01N 2223/612; G01N 23/046; G06T 11/005; H05G 1/64
  See application file for complete search history.

(56) References Cited

U.S. PATENT DOCUMENTS

| | | | |
|---|---|---|---|
| 7,391,927 B2 | 6/2008 | Stierstorfer | |
| 7,920,672 B2 * | 4/2011 | Timmer | A61B 6/4085 378/7 |

FOREIGN PATENT DOCUMENTS

| | | |
|---|---|---|
| DE | 102009030568 B3 | 10/2010 |
| EP | 857337 B1 | 12/2002 |

OTHER PUBLICATIONS

Liang et al. "Iterative image-domain ring artifact removal in cone-beam CT", In: Physics in Medicine and Biology 62, 2017. 5276-5292, (2017).

\* cited by examiner

| measure-ment | repetition parameter | single gain level (s) or plurality of gain levels (M) | signal-to-noise ratio near the center | signal-to-noise ratio remote from the center |
| --- | --- | --- | --- | --- |
| 1 | 10 | s | 67.4 | 74.5 |
| 2 | 50 | s | 78.5 | 80.9 |
| 3 | 350 | s | 82.2 | 82.8 |
| 4 | 10 | M | 65.7 | 72.8 |
| 5 | 50 | M | 78.0 | 80.5 |

FIG. 5

METHOD AND ARRANGEMENT FOR DETECTOR CORRECTION FOR GENERATING OBJECT RADIOGRAPHS

CROSS REFERENCE TO RELATED APPLICATIONS

This application claims priority to German patent application DE 10 2018 201 249.0, filed on Jan. 26, 2018, the entire content of which is incorporated herein by reference.

TECHNICAL FIELD

The invention relates to a method and an arrangement for detector correction for a detector configured for generating object radiographs. In particular, the invention relates to determining a preferred gain and offset correction of such a detector.

BACKGROUND

Radiography apparatuses and methods are used for examining objects and, in particular, for checking workpieces manufactured industrially or by skilled workers. It is thereby possible for example to check and/or ascertain the dimensional accuracy of a workpiece or the presence of internal defects. In particular, use is made of solutions from the field of Computed Tomography (CT), which is based on invasive electromagnetic radiation, in particular in the form of X-ray radiation. X-ray radiation can be generated by accelerating (decelerating) particles (e.g., electrons) in a target of an X-ray radiation source. In this case, the spectral range of the invasive radiation is not limited by specific wavelengths.

In CT apparatuses and methods, a workpiece is irradiated with X-ray radiation from different directions of incidence in order to capture a plurality of radiographs, or in particular X-ray images. These thus represent projection images. The latter are subsequently combined by a computer to form a three-dimensional (3D) representation of the radiographed workpiece.

Detectors including, for example, a scintillator and/or photodiodes are used to record depictions of the radiography, i.e., the radiographs. In particular, the detectors can be configured as so-called flat image detectors, i.e., detectors having a shallow depth. The detectors are generally configured to generate a two-dimensional radiograph from the electromagnetic radiation, which at least partly penetrates through the object or workpiece, and is then incident on the detector. For this purpose, the detectors can include a plurality of individual detector elements, which each generate a respective pixel. The detector elements are often configured in a matrix form with detector elements arranged in rows and columns, which in each case detect a radiation value specific to the element, i.e., a value of the quantity of radiation impinging on the element in the detection time interval. In particular, a gradual radiation value can be detected pixel by pixel, which value can be represented in a corresponding image as a so-called grayscale value of the pixel.

In order to ensure a sufficient quality of the radiographs, the detectors are generally calibrated. In this context, it is known to carry out a detector correction in the form of a gain and offset correction. The offset correction generally serves to compensate for a so-called dark current or a dark voltage of the unirradiated detector by addition or subtraction of a predetermined value (so-called offset value). The offset value, like a gain value, can be determined and/or defined for each detector element and thus pixel by pixel. In particular, the offset value can be added to or subtracted from a grayscale value typically detected pixel by pixel to perform an individual grayscale value correction per pixel. Additionally or alternatively, the offset value can be chosen in such a way as to result overall in as homogeneous a grayscale value distribution as possible in the detected dark image of the detector.

By contrast, the gain correction (or gain factor correction) generally serves to compensate for individual sensitivity deviations of the individual detector elements by an individual multiplier. In particular, for generating a homogeneous radiograph and/or a homogeneous grayscale value distribution, the grayscale values detected pixel by pixel (and if appropriate already offset-corrected) can be obtained by multiplying the raw sensor value with the multiplier.

A so-called bright image can be detected for the gain correction, in the case of which bright image the detector is irradiated without transilluminating an object, e.g., by a homogeneous radiation distribution. Within the scope of the present disclosure, unless excluded by the context, the term radiograph can also be understood to mean such a bright image. Although radiation is not actually transmitted through any object at all in this case, the detector nonetheless generates a two-dimensional image on the basis of the impinging electromagnetic radiation.

Measurement sequences (i.e., the sequences of dark images and/or radiographs) for the gain and offset correction typically include the capture of at least one dark image (for the offset correction) and the capture of at least one bright image (for the gain correction). Even if the detector is not irradiated in the case of a dark image, a dark image, like a bright image, too, can be referred to as a projection image in a simplified manner of expression. After capture of the measurement sequence, in particular the above-explained adaptation of the grayscale values pixel by pixel, image processing can be carried out by known evaluation algorithms to achieve as homogeneous a grayscale value distribution as possible in the images detected in each case. Typically, a plurality of dark and/or bright images are detected, e.g., in order to obtain offset or gain values pixel by pixel by averaging over the respective images. Furthermore, it is possible to pass through a plurality of so-called gain levels, for which bright images are generated with different intensities of the electromagnetic radiation (e.g., in each case with a homogeneous radiation distribution). Each gain level corresponds to an intensity. It is thereby possible to approximate a nonlinear sensitivity curve of the detector elements as a function of the impinging radiation intensity.

The offset and gain values ultimately used for the gain and offset correction may be referred to as setting values for the gain and offset correction. Determining the setting values can be carried out in the context of the measurement sequence explained above (i.e. in the context of capturing at least one bright image and at least one dark image and optionally at least one bright image per gain level).

Unless indicated or evident otherwise, all of the general explanations above also apply to the present invention.

When creating object radiographs, it is possible for artefacts to arise, i.e., effects which are discernible in the image and which do not correspond to the actual radiation distribution impinging on the detector. If a plurality of images are detected at different directions of incidence in the manner of a CT method, wherein the different directions of incidence correspond to a rotation of the object relative to the detector and the radiation source about a rotation axis, in particular so-called ring artefacts may arise. The latter are discernible in the reconstructed three-dimensional representation of the radiographed object as ring-shaped structures extending around the rotation axis, without the object itself having such ring-shaped regions.

A first insight of the invention is that with a precise gain and offset correction such ring artefacts can be reduced or even entirely avoided.

However, since this correction requires a certain time, during which the object radiography arrangement cannot be used for object radiography actually intended, the gain and offset correction cannot be extended arbitrarily in terms of time. Moreover, it may be difficult to suitably choose the parameters for the measurement sequence for the gain and offset correction (e.g., the number of bright images and/or of dark images and/or the number of bright images per gain level or for individual gain levels). If unsuitable parameters are chosen for a specific detector, losses of precision or an unnecessary delay of the capture and evaluation of the captured images may occur. Hitherto, extensive experience has been necessary, therefore, in order to suitably choose the parameters of such measurement sequences.

SUMMARY

It is an object of the invention to enable a gain and offset correction of a detector that is as precise as possible but saves as much time as possible.

The invention generally provides for evaluating the quality of a result of the capture of at least one projection image of a test object and in particular a sequence of projection images of the test object (for example with regard to the extent of possible ring artefacts) to draw a conclusion about the quality of the gain and offset correction. By repeatedly implementing a gain and offset correction and evaluating the image quality respectively obtained in the process, it is thus possible to determine a preferred gain and offset correction. Typically, this is carried out whilst modifying a measurement sequence for the gain and offset correction, such that information concerning the image quality obtained in the process is present in each case for a plurality of different setting values (i.e., for different offset and/or gain values). A particularly suitable or optimum gain and offset correction can then be determined therefrom.

In detail, a method for detector correction for a detector configured for generating object radiographs is provided. The detector correction is a gain and offset correction. The detector can be a flat image detector and/or can be configured to detect electromagnetic radiation, and in particular X-ray radiation. In accordance with the introductory explanations, the object radiographs generated can also include only dark and/or bright images for which radiation is not transmitted through any object, rather the detector is irradiated directly. The detector can be part of an object radiography arrangement, and in particular of a CT arrangement to generate three-dimensional representations of an object, such as, a workpiece manufactured industrially and/or by skilled workers.

The method includes the following steps:

a) providing a detector having setting values for a gain and offset correction;

b) capturing a plurality of object radiographs of a test object by the detector and reconstructing a three-dimensional representation of the test object on the basis of the object radiographs;

c) determining at least one quality value of the reconstructed three-dimensional representation;

d) repeating steps b) and c) at least once, wherein before the repetition, a parameter set is generated and a measurement sequence is implemented on the basis thereof, at least one setting value for the gain and offset correction of the detector being determined anew on the basis of the measurement sequence; and e) determining a preferred gain and offset correction of the detector on the basis of the plurality of quality values determined overall.

As mentioned, the setting values of the gain and offset correction can include an offset value and/or a gain value, in particular pixel by pixel, in order to correct the raw values of the detector values of the detector on the basis thereof. The setting values can be stored in a storage and/or control unit of the detector or an arrangement including the detector. The test object can be a predetermined object having typical properties for carrying out calibration processes (such as, the gain and offset correction). In particular, the test object can be configured as homogeneously as possible and/or can have a density as homogeneous as possible. Furthermore, the test object can have at least one axis of symmetry, but typically at least two or three axes of symmetry extending at an angle with respect to one another. The test object can be produced from a metal material, and include aluminum, in particular. In one variant, the test object is configured as a cylinder, typically as a solid cylinder. The cylinder can have an oval or circular cross-sectional area, which is typically constant along its length. The test object can generally be different from the objects and/or workpieces provided for an actual object checking. However, it can also be chosen to be identical thereto.

The object radiographs can be generated by radiographing or transilluminating the test object from different directions of incidence. In particular, a relative movement of a radiation source and the test object can be provided, for example, in the manner of known CT scanning arrangements. The object radiographs can correspondingly be generated for different relative arrangements of radiation source and test object. Customary evaluation algorithms can be used for reconstructing the three-dimensional representation from the object radiographs.

The quality value can generally concern a value that makes it possible to draw a conclusion about the quality of the gain and offset correction. By way of example, it can be a value relating to the homogeneity of the image values of the reconstructed representation, in particular in spatial regions having a uniform density of the test object. The term "spatial regions" does not exclude the quality value being determined exclusively or else in a region of a two-dimensional section through the reconstruction volume. In particular, sections perpendicular to a rotation axis about which the test object is rotated relative to the detector are suitable in order to enable the different radiography directions.

Additionally or alternatively, the quality value can concern a freedom from image disturbances or artefacts in at least selected regions of the reconstructed representation. The image disturbances can be, for example, contrast, chromatic or brightness aberrations. The latter can form a noise component explained below. As likewise explained below, the quality value can indicate in particular the extent of possible ring artefacts within the reconstructed representation.

For repeating the 3D reconstruction, the parameter set can be generated to result in a measurement sequence that possibly differs from the previous and typically from each previous measurement sequence for determining setting values for the gain and offset correction. The measurement sequence can be understood to mean capturing, as mentioned in the introduction, dark and/or bright images for the gain and offset correction, including possible repeated image capturescaptures for the purpose of averaging and/or for the purpose of an image detection for different gain levels. To put it differently, before the repetition of steps b) and c) (and typically before each repetition thereof), a renewed gain and offset correction of the detector can be implemented, which differs from previous gain and offset corrections, in particular with regard to the measurement sequence carried out therefor.

If the measurement sequences deviate from one another, other expected setting values are also determined in each case for the gain and offset correction. Consequently, it is possible to generate a plurality of reconstructed three-dimensional representations for different gain and offset corrections and to implement a corresponding quality value determination for each of the representations.

In accordance with some exemplary embodiments, only a single number of dark images is considered, such that the offset correction is carried out only on the basis of this single number of dark images. In the context of the method, therefore, the offset value can also be determined only once and taken as a basis for all repetitions in accordance with step d). Determining the setting values anew in step d) can thus be restricted to determining the gain value anew, and not the offset value as well, wherein this can in turn be implemented for different gain levels.

To summarize, provision can thus be made for changing at least one setting value for the gain and offset correction before a repetition of steps b) and c), which can be carried out indirectly by changing the measurement sequence for determining the setting values for the gain and offset correction. Thereafter, an image capturing and 3D reconstruction are carried out once again on the basis of the resulting changed gain and offset correction of the detector. The 3D reconstruction is thereupon evaluated with regard to its quality.

Determining a typical gain and offset correction is subsequently carried out on the basis of the determined quality values for the plurality of 3D reconstructions. This can include in particular determining preferred setting values for the gain and offset correction which are intended to be used for a subsequent actual object or workpiece checking. As typical gain and offset correction, it is possible to determine that gain and offset correction (or the associated setting values thereof) for which the best quality values are achieved (for example a maximum quality value). Provision can likewise be made for determining the preferred gain and offset correction computationally. This can be carried out for example on the basis of an interpolation of setting values by which an image detection and quality value determination were actually carried out.

Generally, all method steps can be implemented automatically. The change from step d) to b) and thus between a measurement sequence for the gain and offset correction (i.e., the generation of dark and/or bright images, typically without a test object in the beam path) and the transillumination of a test object may however require guiding the test object into and/or out of an object receiving region or object radiography region of the arrangement. The latter can be carried out manually, but also automatically.

The method is generally distinguished by the fact that a user can carry out with little effort and comparatively rapidly a substantially or even completely automatic determination of suitable setting values for the gain and offset correction.

Contrary to previous solutions, therefore, the user need no longer to rely on proceeding on the basis of empirical values. Instead, by way of the quality values determined, a quantifiable variable is provided directly which makes it possible to deduce the quality of the image detection for different gain and offset corrections, and thus generally suitable correction setting values.

The inventor has additionally recognized that varying and determining setting values for the gain and offset correction by way of actual measurement sequences yields to precise results. This is firstly owing to the fact that the alternative of directly predefining or calculating setting values for the detector correction may be impractical and imprecise. In particular, it may be difficult to foresee what measurement sequence parameters (let alone setting values for the gain and offset correction) yield to the best results for a specific detector.

By way of example, it has been determined that for detectors which have a substantially linear sensitivity curve, measurement sequences may be advantageous for which only one gain level is considered, but a comparatively large number of bright image detections and thus averagings are carried out therefor. If, instead, a large number of gain levels are considered for such linear detectors, the gain and offset correction may be corrupted on account of outliers and a comparatively long period of time is required for capturing the images. However, if the detector has a substantially nonlinear sensitivity curve, considering only one gain level may be inadequate.

However, estimating beforehand what detector has what sensitivity curve, and moreover depending on predetermined ambient and in particular temperature conditions, is possible only with difficulty. For this reason, too, the method affords the advantage of taking account of different possible detector characteristics (and in particular different possible sensitivity curves) by repeating the measurement sequences for determining setting values for the gain and offset correction. On the basis of the quality values determined and with knowledge of the associated gain and offset correction or the measurement sequence carried out therefor, it is then possible to deduce what type of sensitivity curve the detector most likely has. Overridingly, the method according to an aspect of the invention thus makes it possible to ensure that suitable setting values for the gain and offset correction are determined to the greatest possible extent automatically for a specific detector.

According to an aspect of the method and arrangement, the parameter set includes at least one of the following parameters:
  a dark image parameter defining the number of dark images to be captured;
  a gain parameter defining the number of gain levels (and/or the type thereof or the intensity per gain level) for detecting bright images; and
  one or a plurality of repetition parameters defining the number of bright image captures per gain level or in each case for an individual gain level.

All of these parameters can be used to define the measurement sequence for determining the setting values for the gain and offset correction. The measurement sequence may generally be distinguished by the fact that it is defined exclusively by way of the abovementioned parameters, and in particular all of the abovementioned parameters. According to an aspect of the invention, the dark image parameter remains invariable or is even set to zero during a repeated implementation of the measurement sequence in accordance with step d), such that only the gain parameter and/or the repetition parameter are/is varied or have/has a value different from zero.

A dark image can be understood to mean the image detection by the detector in the absence of irradiation, as explained in the introduction. By contrast, a bright image can be generated by irradiating the detector and typically in the absence of an object to be transilluminated, wherein the irradiating can be carried out with a predetermined intensity that is different from zero.

In this context, a gain level can concern a predetermined intensity value that is used for generating a corresponding bright image. If only one gain level is used, then this typically involves the maximum intensity with which the detector can be irradiated.

Implementing repeated bright image detections by the repetition parameter can be provided for an averaging of the measurement results. By way of example, suitable setting values for the gain and offset correction can be determined from each of the bright images and subsequently be averaged.

Overridingly, the determined setting values for the gain and offset correction can be defined depending on an intensity of the radiation used for the radiography. This applies in particular to the gain value determined. If the detector has an (assumed) nonlinear sensitivity curve, it may be advantageous to determine and/or to store the gain values depending on the impinging radiation intensity. In this case, the provision of a plurality of gain levels as explained above is furthermore appropriate in order to be able to approximate the possible nonlinear sensitivity curve of the detector. The gain and offset correction can thus include storing the setting values (i.e., an offset and gain value) which can subsequently be used for a typical pixel-by-pixel grayscale value correction of the detected object radiographs.

Generating the parameter set can be implemented by a control device of an object radiography arrangement including the detector. The parameter sets can be stored beforehand and read out as necessary. Alternatively or additionally, the parameter sets can be calculated before or in the course of carrying out the method (or each time step d) is implemented).

In a further exemplary embodiment of the method and of the arrangement, the gain and offset correction in step a) is carried out on the basis of initial setting values. The initial setting values can be stored beforehand as typically fixed initial values, e.g., in a control device of an arrangement including the detector. In particular, the values may be previously stored default values that are predefined and stored, e.g., by a manufacturer of a corresponding arrangement. In this context, provision can furthermore be made for choosing the parameter set in step d) in such a way that setting values that deviate from the initial setting values are determined in the context of the measurement sequence. With knowledge of the initial setting values, such a deviation can be achieved by way of a suitable choice of the parameter set. Particularly in the case of a typical pixel-by-pixel gain and offset correction in which the setting values can also be determined individually for each detector pixel, it may be assumed with a high probability that the definition of a separate parameter set results in setting values that deviate from the initial setting values. Additionally or alternatively, the desired deviation can also be achieved by setting the dark image parameter and/or the gain parameter to a value of more than 1.

As an alternative thereto, the gain and offset correction in step a) can be carried out on the basis of initially carrying out a measurement sequence for determining setting values for a gain and offset correction. The measurement sequence can include determining dark and bright images as discussed above (if appropriate also for a plurality of gain levels). In the case of this aspect of the invention, provision can accordingly be made for completely implementing a corresponding measurement sequence at the beginning of the method in order to determine initial setting values for the gain and offset correction. On the basis thereof it is possible to carry out an image detection and 3D reconstruction.

When already initially carrying out a measurement sequence, provision can furthermore be made for choosing the parameter set in step d) in such a way that a deviating measurement sequence by comparison with step a) is implemented. By way of example, for this purpose, it is possible to vary one of the above-explained parameters of the parameter set by comparison with the initial measurement sequence from step a). If provision is made of a plurality of repetitions in accordance with step d), provision can furthermore be made, upon each repetition, for implementing a measurement sequence that differs from the previous repetitions in accordance with step d) and a possible measurement sequence from step a).

Overall, it is thereby possible to ensure that the meaningfulness of the method results obtained is increased since the gain and offset corrections are in each case determined under deviating conditions and are implemented on the basis of deviating setting values.

Overridingly, in the case of the method and the arrangement, provision can also be made of a plurality of repetitions in accordance with step d), wherein the parameter set is generated before a repetition in each case in such a way that a deviating measurement sequence in comparison with the repetitions already carried out is implemented. As indicated above, this in turn makes it possible to increase the meaningfulness of the results ultimately obtained, since as many different gain and offset corrections as possible are taken into account. Furthermore, it is thereby possible to prevent the implementation of redundant measurement sequences and to reduce the method duration required overall.

According to a further aspect of the arrangement and of the method, provision is made for the offset value to be determined only once and in particular not to be determined anew upon each repetition of step d). In particular, a former number of dark images detected for a former gain and offset correction of the detector can also be taken as a basis at least partly for a repeated gain and offset correction in accordance with step d). By way of example, provision can be made for detecting only a single number of dark images and taking the latter as a basis for the entire method. The number of dark images (which can also be just one) can be generated or detected for example in the context of step a), in particular in the context of a measurement sequence carried out in this case. Alternatively, it is possible to generate the number of dark images in the course of carrying out for the first time a measurement sequence in accordance with step d). By reducing the number of detection processes for the dark images for the gain and offset correction, it is possible to reduce the method duration required overall. In the context of step d), it is thus possible to carry out only a determination of the gain value as a corresponding setting value.

In a further exemplary embodiment of the arrangement and of the method, if a repetition in accordance with step d) involves once again passing through a formerly already detected gain level, the bright images formerly detected for this gain level are taken as a basis at least partly for the gain and offset correction in step d). By way of example, after generating and in particular varying the parameter set in step d), it is possible to determine whether the parameter set includes a gain level already passed through during a former repetition (or during a possible initial measurement sequence in step a)).

In this case, passing through a gain level can be understood to mean determining at least one bright image for this gain level. If the above checking reveals that a gain level is passed through once again by comparison with former measurement sequences, the bright images already generated for this gain level can be taken into account once again completely or at least partly in the repetition in accordance with step d). The bright images can then be evaluated with further bright images determined for this gain level in the context of currently carrying out step d) for determining the setting values for the gain and offset correction or completely replace a possible bright image detection. This measure, too, can contribute to reducing the method duration required overall.

According to one aspect of the arrangement and of the method, the quality value indicates the extent of ring artefacts in the reconstructed three-dimensional representation. In particular, the quality value can quantify the extent and/or generally enable the corresponding extent to be deduced. The quality value can be, e.g., the number or spatial density of ring artefacts in a predetermined region of the reconstructed three-dimensional representation (for example in a predetermined sectional view or plane of the representation). A ring can be identified as such, e.g., if, in an evaluation direction extending, e.g., in a sectional plane perpendicular to an axis of rotation of the arrangement, or in a plurality of evaluation directions (for example a plurality of radial directions proceeding from the center of a cross section), a grayscale value within a region in the evaluation direction having a predefined length changes by more than a predefined absolute value. Other possibilities for ascertaining a ring exist. By way of example, it is possible to carry out evaluation not just along one evaluation direction, but along a plurality of evaluation directions each intersecting the axis of rotation. Alternatively or additionally, instead of the predefined values (length and absolute value) mentioned, it is possible to consider a smoothed or non-smoothed profile of the grayscale values in the evaluation direction and/or to form at least one spatial derivative of the grayscale value. If the first spatial derivative is greater than a predefined threshold value and/or if the second spatial derivative is zero, a decision can be taken that a ring artefact is situated at the respective location.

Additionally or alternatively, it is possible to specify a maximum or averaged distance between adjacent ring artefacts. In the context of the present disclosure, determining the quality value can be carried out manually by an operator, e.g., by observing a corresponding sectional view or plane of the reconstructed three-dimensional representation. Typically, however, determining the quality value is carried out automatically, and for example by a suitable image evaluation algorithm (e.g., as described above).

In order to eliminate ring artefacts, in previous CT methods, additional relative movements between the object to be transilluminated and the radiation source are often provided during the image detection. By way example, the axis of rotation about which the radiation source and the object are moved (or rotated) relative to one another can be displaced in at least one dimension. However, this increases the requirements made of a subsequent 3D reconstruction from the plurality of object radiographs detected overall. Moreover, it is necessary to ensure a sufficiently high positioning accuracy for the displacement of the axis of rotation. It has been found that with this variant, therefore, it is not always possible to achieve a sufficient measurement accuracy. Moreover, the additional movements increase the measurement time required overall, which is disadvantageous in particular for measurement processes integrated into a production line (so-called inline CT scanning).

Consequently, one insight of the invention also consists in the fact that ring artefacts can instead be eliminated by a gain and offset correction that is as precise as possible. By virtue of the fact that a correspondingly precise selection of setting values for the gain and offset correction, which selection is particularly suitable in particular for a specific type of detector, is carried out with the method and the arrangement according to an aspect of the invention, it is thus also possible to reduce the ring artefacts in the finally reconstructed three-dimensional representation. On the other hand, the extent of the remaining ring artefacts allows a current achieved quality of the gain and offset correction to be deduced.

According to a further aspect of the arrangement and of the method, the quality value is determined on the basis of a signal-to-noise ratio in the reconstructed three-dimensional representation.

Noise is understood to mean a deviation of measurement values that is based on random processes, e.g., on account of thermal, electrical or photonic disturbance influences. In particular, the noise in the present case may arise, therefore, as a result of the detector and as a result of disturbing radiation such as stray radiation, for example.

The signal-to-noise ratio (SNR) is a measure of quality for a used signal on which a noise signal is superimposed, and can be formed in particular by the quotient of a mean value of the signal intensity and a standard deviation at the signal intensity. In principle, the mean value can be formed in various ways and/or some other variable describing the statistical variation can be used instead of the standard deviation, such that various procedures exist for calculating the SNR. The statistical deviation, for example the standard deviation, can be formed in particular from the change in a signal value, e.g., a pixel, over time or from the spatial deviation and/or variation of the signal value, e.g., from a defined number of pixels which belong to the same mean value of the signal intensity.

In this case, too, the quality value can once again be considered for a selected sectional view or plane (e.g., a plane perpendicular to the axis of rotation) of the representation. Generally, the signal-to-noise ratio can yield at least indirectly conclusions about the extent of ring artefacts. Consequently, the signal-to-noise ratio can be used as a quality value indicating the extent of ring artefacts.

The signal-to-noise ratio can be obtained by forming a quotient of a signal or used portion and a noise portion at the detected radiograph. The noise portion can be formed by determining and summing pixels or image regions that deviate unusually from adjacent pixels or from adjacent image regions (for example with regard to their color or with regard to the grayscale value). The used portion can be formed by determining and summing pixels or image regions that do not deviate unusually from adjacent pixels or image regions (for example with regard to their color, intensity and/or brightness).

The signal-to-noise ratio can alternatively be calculated as a (e.g., quadratic) deviation of the individual image values of the pixels from their average value. Here the average should be calculated in each case over the image region considered.

In this context, provision can furthermore be made for the signal-to-noise ratio to be determined for different regions of the reconstructed three-dimensional representation (for example by a comparison thereof). In particular, it is possible to consider different regions in a common sectional view or plane of the representation. According to an aspect of the invention, the signal-to-noise ratio is determined for a first region, which images a region of the test object that is near the center (near the axis of rotation and thus near the center of rotation) and for a second region, which images a region of the test object that is remote from the center. The terms "near" and "remote" should be understood to mean that the regions are at distances of different magnitudes from the center, i.e., from the axis of rotation. Instead of "near the center" and "remote from the center", it is therefore also possible to talk of "nearer the center" and "more remote from the center". In particular, the region remote from the center can be at a distance from the center that is greater by a predefined absolute value compared with the region near the center. The region remote from the center can be, for example, an in particular radial edge region of the test object.

It goes without saying that it is also possible to consider further regions which can likewise be arranged at a distance and preferably a radial distance from the region near the center.

The plurality of regions or the signal-to-noise ratios determined therefor can then be evaluated for determining a common quality value. In this case, the quality value can concern or be formed from a difference between the signal-to-noise ratios of the first and second regions or a quotient of the ratios. A small difference or a quotient near the value 1 indicates a homogeneous three-dimensional representation, and in particular the absence of possible ring artefacts. This last can be used in the context of method step e) in order to determine that gain and offset correction (or the associated setting values) for which a quality value having a preferred or optimum value was determined (i.e., in step e) it is possible to select the correction with which the quotient closest to the value 1 or the smallest difference is achieved).

In a further exemplary embodiment of the apparatus and of the method, at least one repetition in accordance with step d) is implemented with only one gain level and at least one repetition in accordance with step d) is implemented with more than one gain level. In the case of the repetition with only one gain level, provision can additionally be made for a repetition parameter of greater than 1 to be chosen, for example a repetition parameter of 10. In the case of the repetition with more than one gain level, by contrast, provision can be made for providing a smaller repetition parameter in comparison with the repetition with only one gain level, for example a repetition parameter of only 1 or 2. According to this aspect of the invention, it is ensured that both a possible linear and a possible nonlinear sensitivity curve of the detector can be detected by a corresponding measurement sequence. Depending on which of the above variants yields a better quality value, the presence of a corresponding linear or nonlinear sensitivity curve can then be deduced.

The invention furthermore relates to an object radiography arrangement comprising
  a detector configured to generate object radiographs;
  a radiation source configured to direct invasive electromagnetic radiation onto the detector;
  an evaluation unit configured to determine a quality value of a three-dimensional representation reconstructed from the object radiographs; and
  a control device configured to control the arrangement for implementing a method according to the aspects above or below.

The radiation source can be an X-ray radiation source. The detector can be configured in accordance with any of the above aspects of the invention.

The control device can be configured, in particular, to cause the detector and the evaluation unit to detect corresponding bright and/or dark images for the gain and offset correction. Likewise, the control device can be configured to generate parameter sets for measurement sequences for determining setting values for the gain and offset correction and/or to vary such parameter sets by comparison with measurement sequences already carried out.

The evaluation unit can include a computing unit (e.g., in the form of a CPU or a computer) and/or determine the quality value by suitable image evaluation algorithms. However, provision can also be made for an arrangement, as generally defined above, not to include an evaluation unit and for determining the quality value to be carried out manually, e.g., by manually evaluating (for example counting) possible image disturbances in the reconstructed three-dimensional representation.

Finally, the arrangement in principle can be configured to carry out a CT method and/or be operable in the manner of a CT scanner, for example by relative movements of radiation source and detector.

It goes without saying that the arrangement can include any further feature and any further unit or device in order to provide all of the method steps, effects or interactions above or below.

In order to afford a better understanding of the invention, a few further technical terms are explained below:

A grayscale value is a numerical value which is assigned to each pixel in a two-dimensional image or to each voxel in a computed tomography image (three-dimensional) and corresponds to a specific signal intensity. If a pixel or a voxel is represented in black, this means that the associated grayscale value has the absolute value of zero. In a projection image (detector image), such a pixel represents a radiation below a detection limit at the position of the pixel. If a pixel or voxel is represented in white, this means that the associated grayscale value has a maximum absolute value. At least the highest detectable radiation was present at the position corresponding to the position of the pixel in a projection image. In the reconstructed volume, by contrast, a higher grayscale value corresponds to a higher attenuation of the radiation than a lower grayscale value.

Beam hardening is a variation of the spectrum of polychromatic X-ray radiation upon penetrating through matter. With increasing penetration depth, more and more X-ray quanta or photons having relatively low energy are scattered by the matter, with the result that the proportion of photons having higher energy increases in the radiation passing through the matter rectilinearly. This means that the average energy or hardness of the radiation increases. This is tantamount to a shift in the spectrum toward a higher absolute value of energy; this phenomenon is referred to as beam hardening. In computed tomography, beam hardening occurs as a disturbing effect that can lead to so-called hardening artefacts.

An artefact is a disturbing image constituent (image aberration) that does not describe the geometry and the weakening of an object examined by X-ray radiation and is also not caused by noise.

Ring artefacts are artefacts manifested as concentric rings.

A beam hardening artefact is an artefact caused by the variation of the spectrum of X-ray radiation when penetrating through an object being examined. In the case of objects including plastics parts and metal parts, dark, ray-shaped artefacts superimposed on the plastics parts arise upon penetration of X-ray radiation between the metal parts. Objects that strongly absorb X-ray radiation, in particular objects including metal parts, appear inhomogeneous in the reconstructed image, even though in reality they have a homogeneous density. The surrounding air likewise appears inhomogeneous. A beam hardening artefact occurs particularly in the case of an object in which X-ray radiation penetrates through the object with a relatively large depth. At the outer edge of an object region of homogeneous density, the object in a CT image appears to be brighter and thus denser than in a region located further inward.

BRIEF DESCRIPTION OF THE DRAWINGS

The invention will now be described with reference to the drawings wherein.

DESCRIPTION OF EXEMPLARY EMBODIMENTS

Figure 1:
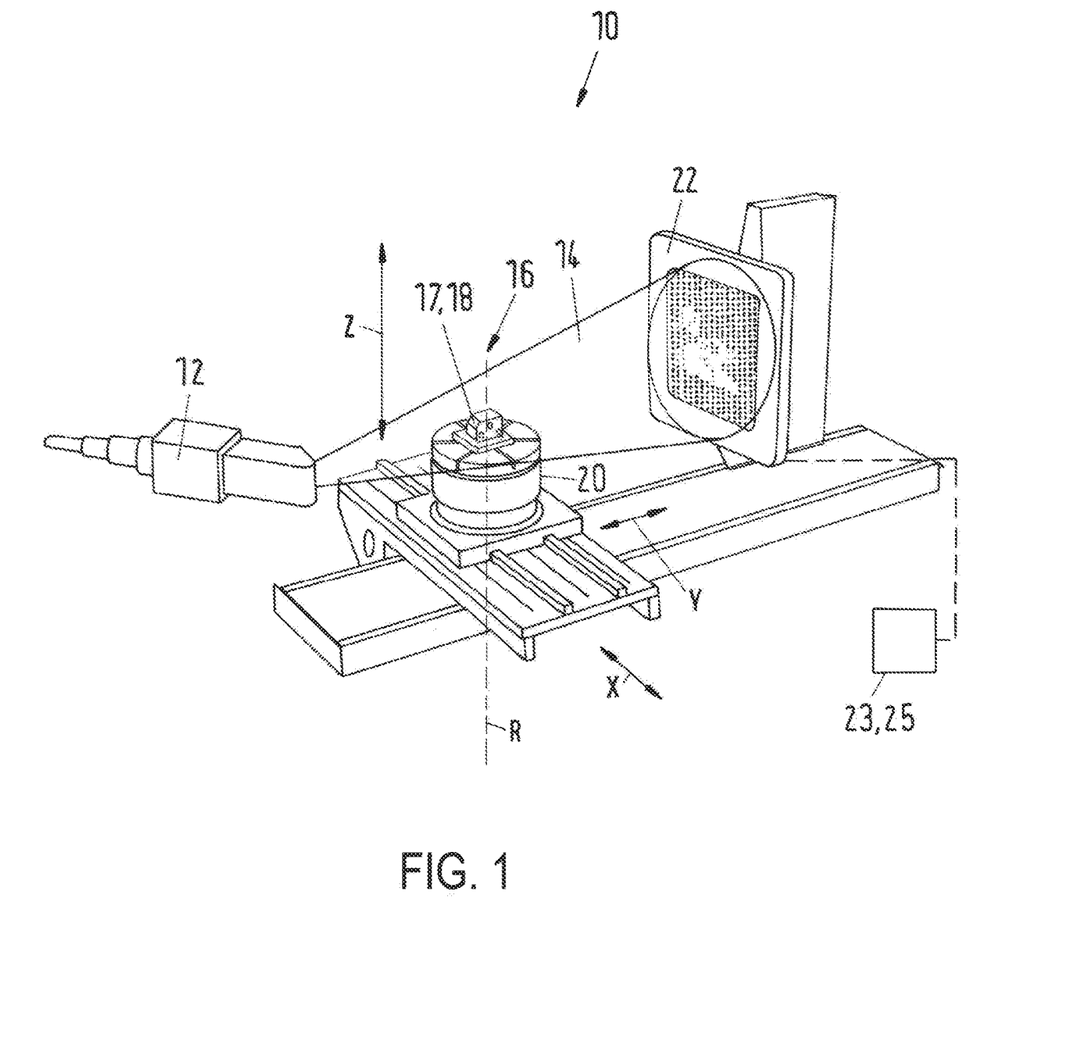
FIG. 1 illustrates an arrangement with which a method is implementable according to an exemplary embodiment of the invention.

The arrangement 10 in accordance with FIG. 1 includes a stationary radiation source 12, which emits X-ray radiation in the form of a beam cone 14. The beam cone 14 passes through an object receptacle region 16, in which an object 17 to be transilluminated in the form of a workpiece 18 is arranged. Alternatively, not just with regard to this exemplary embodiment but generally in association with the present disclosure, instead of a beam cone, a deformed, non-rotationally symmetrical beam cone, a pyramidal radiation region or a differently shaped radiation region can be involved, within which the invasive radiation proceeding from the radiation source extends to the detector. In the exemplary embodiment, the workpiece 18 is positioned on a rotary table 20, such that it is rotatable about a vertically extending axis of rotation R. The rotary table 20 is furthermore height-adjustable, as indicated by the vertical axis Z in FIG. 1. Furthermore, there exist two horizontal axes X, Y in order to be able to position the rotary table 20 in the horizontal plane.

After passing through the object receptacle region 16, the beam cone 14 impinges on a detector 22, which is configured as a flat image X-ray detector. The detector 22 is configured in a manner known per se to generate a two-dimensional radiograph of the workpiece 18 from the impinging radiation. For this purpose, the detector 22 includes a matrix-type arrangement of a plurality of pixels at its front surface facing the observer in FIG. 1. The pixels each detect a dedicated radiation value (or a so-called grayscale value), which in turn is used as an individual image point for generating the radiograph.

The arrangement 10 is operable in the manner of a CT scanner. In detail, the workpiece 18 is able to be arranged at different relative positions with respect to the radiation source 12 by rotation about the axis of rotation R, such that the X-ray radiation is able to be directed onto the workpiece 18 from different directions of incidence. An object radiograph is generated for each rotational position or relative arrangement. The plurality of these images is subsequently used in a manner known per se for a reconstruction of a three-dimensional representation of the workpiece 18.

The method according to an exemplary embodiment of the invention provides for subjecting the detector 22 to a gain and offset correction that is as precise as possible, for example in order to avoid ring artefacts in the reconstructed three-dimensional representation. In particular, the gain and offset correction is intended to enable as precise approximation as possible to properties of the detector 22 (for example whether the latter has a linear or nonlinear sensitivity curve), which properties are generally not known or are known only approximately. In this case, the method according to the exemplary embodiment of the invention is configured in such a way that a comparatively short time duration is required relative to the achievable quality of the gain and offset correction.

This is explained below with reference to the flowchart in FIG. 2. The method begins with step S1, which involves providing a detector 22 having setting values for a gain and offset correction. The setting values may be stored in a control device 23 of the arrangement 10, which is connected to the detector 22 (see FIG. 1). Although not illustrated by corresponding signal lines in FIG. 1, the control device 23 can also be used to control the radiation source 12 (for example selectively to activate or to deactivate it and/or to control the intensity of the X-ray radiation emitted by it). Furthermore, the control device 23 can be configured to control all positioning and rotation axes R of the arrangement 10.

In step S1, the setting values include an offset value predefined pixel by pixel for compensating for an individual dark current per pixel. Furthermore, the setting values include a gain value predefined pixel by pixel in order to correct the individual sensitivity of each pixel. A grayscale value detected by an individual pixel of the detector 22 can thus be corrected by addition or subtraction of the offset value, wherein the resulting intermediate value is subsequently multiplied by the gain value. Overall, a plurality of pixel-specifically corrected grayscale values is thus obtained, from which the final object radiograph is established.

The setting values in step S1 can be predefined as initial setting values for example by a manufacturer of the arrangement 10 or of the detector 22. They can thus be setting values which ensure a sufficient gain and offset correction with a certain probability. However, with such initial setting values, it is not possible to take account of real process conditions such as actual temperature profiles and/or aging phenomena of the detector 22.

Alternatively, therefore, the initial setting values can also be obtained by implementing in step S1 a first initial measurement sequence for obtaining the setting values. Such a measurement sequence is explained in greater detail below and generally affords the possibility of taking account of the real ambient conditions and also the current state of the detector 22 and thus of achieving a possibly more precise gain and offset correction.

Subsequent step S2 then involves capturing a plurality of object radiographs by the gain- and offset-corrected detector 22. For this purpose, the workpiece 18, (cf. FIG. 1), is replaced by a cylindrical test object 24, which is explained below, and which is likewise positioned on the rotary table 20 (cf. FIG. 3D). The object radiographs are generated by way of the above-explained rotation of the test object 24 about the axis of rotation R and the accompanying variation of the direction of incidence of radiation. A three-dimensional representation of the test object 24 is reconstructed from this plurality of object radiographs. This is carried out by customary CT reconstruction algorithms.

Thereafter, in step S3, the reconstructed 3D representation is checked with regard to its quality. This can be carried out by an evaluation unit 25, which is integrated into the control device 23 in the case of the exemplary embodiment shown in FIG. 1. In this example exemplary embodiment, a quality value is determined that quantifies the extent of ring artefacts 26 in the reconstructed three-dimensional representation (cf. FIG. 3A). The inventor has recognized that the extent of the ring artefacts 26 enables a conclusion to be drawn about the quality of the gain and offset correction. In particular, the extent of the ring artefacts 26 can be reduced by a gain and offset correction that is as precise as possible and that is adapted to the detector 22 and also the concrete ambient conditions. One variant for determining the quality value is explained in greater detail below with reference to FIG. 4. The quality value is stored for each 3D reconstruction and together with the setting values used here for the gain and offset correction in the control device 23 from FIG. 1 (cf. FIG. 5).

A renewed image detection and 3D reconstruction are prepared in subsequent step S4. For this purpose, the control device 23 generates a parameter set in order to implement a measurement sequence for determining new setting values for the gain and offset correction of the detector 22. In this case, the parameter set can be generated in accordance with user inputs or general computation and/or variation rules. Likewise, the parameter set may be stored beforehand in a storage unit and be read out therefrom. In the exemplary embodiment shown, the parameter set includes all parameters for predefining the measurement sequence and varying it relative to possible previous measurement sequences.

A measurement sequence for determining the setting values generally includes capturing a specific number of dark images, for which the detector 22 is not irradiated but nevertheless performs an image detection. This serves for determining an offset value for each pixel, wherein the offset value is chosen in such a way that the grayscale value distribution in the dark image(s) turns out to be as homogeneous as possible in each case. If a plurality of dark images are detected, the offset values detected for each dark image can subsequently be averaged. The parameter set for defining the measurement sequence thus includes a dark image parameter defining the number of dark images to be detected.

Furthermore, the measurement sequence includes capturing a specific number of bright images, for which the detector 22 is irradiated with X-ray radiation having a predetermined intensity. When detecting the bright images, radiation is typically not transmitted through any object 17, and in particular not through any test object 24 either. This serves for determining the gain value for each pixel, wherein the gain value is generally chosen in such a way that the grayscale distribution in the bright image(s) turns out to be as homogeneous as possible.

In this case, provision can furthermore be made for considering only one intensity of the X-ray radiation, which corresponds to considering only one so-called gain level. Alternatively, provision can be made for generating bright images for a plurality of intensities of the X-ray radiation (that is to say for a plurality of gain levels). The parameter set thus also includes a gain parameter defining the number (and, if appropriate, the type or the intensity value) for the gain levels to be taken into account. Furthermore, the parameter set includes a repetition parameter defining the number of bright image detections per gain level. If provision is made of a plurality of bright image detections for a gain level, it is possible once again to carry out an averaging of the gain values detected overall for this gain level.

Step S4 accordingly involves generating a parameter set including the dark image parameter, the gain parameter and the repetition parameter explained above. A complete measurement sequence for determining anew the setting values for a gain and offset correction of the detector 22 is then implemented on the basis of the quality value. At the end of step S4, new gain and offset values (i.e., new setting values) are thus present for the detector 22 and are stored in the control device 23.

The method thereupon returns to step S2, in which the detector 22, on the basis of the new setting values for the gain and offset correction, performs a renewed detection of a plurality of object radiographs, on the basis of which a renewed three-dimensional representation of the test object 24 is reconstructed. This new reconstructed representation that was created on the basis of the gain and offset correction changed relative to the initial pass is subsequently examined more closely in step S3 in order to determine an associated quality value.

Thereafter, the method returns again to step S4, which involves generating a new parameter set and once again passing through a measurement sequence for determining new setting values for the gain and offset correction. On the basis of these new setting values, steps S2 and S3 are then repeated in order to generate a further three-dimensional representation of the test object 24 on the basis of the corresponding new gain and offset correction. The loop includes steps S4, S2 and S3 can be repeated as often as desired, but in any case is implemented at least once.

As a result, therefore, for a plurality of reconstructed three-dimensional representations that were generated in each case on the basis of a specific gain and offset correction of the detector 22, the quality values determined therefor are present. The corresponding method result or the information determined overall is summarized in the table in FIG. 5. As explained below with reference to FIG. 5, a typical gain and offset correction can be determined from such a table in step S5 from FIG. 2, and is subsequently used for actual object or workpiece radiography.

For the above method sequence from FIG. 2, firstly a few further aspects of the exemplary embodiments according to the invention are discussed below.

If an initial measurement sequence for determining the initial setting values is provided in step S1, the parameter set can be defined in step S4 in such a way that a measurement sequence deviating from step S1 is implemented. The intention is thereby to avoid the determination of redundant reconstructed representations and possibly redundant quality values and to reduce the method duration.

If step S4 is implemented a number of times, for the same reason provision can be made for defining the parameter set in each case in such a way that no repetition of measurement sequences that have already been implemented arises.

If detection of dark images had already been performed in step S1, at a subsequent point in time and in particular upon implementing step S4 for the first time, it is possible to dispense with performing a dark image detection again. The dark image parameter can therefore be set to zero. In other words, provision can be made, in the context of the method, for performing a dark image detection and thus a determination of the offset value only once and then concentrating on determining the gain value under typically variable measurement sequences. Consequently, in accordance with step S4, provision can also generally be made for determining only a single setting value of the gain and offset correction in the form of the gain value, whereas the offset value is assumed to be constant after having been determined once.

If step S1 did not involve implementing a measurement sequence with detection of dark images, but rather reading out the initial setting values from a memory, for example, the dark images can only be detected when step S4 is implemented for the first time. The offset value can then likewise only be determined when this step is implemented for the first time.

If, when implementing step S4, the parameter set is defined in such a way that the measurement sequence contains a gain level already passed through at a previous point in time (for example during a possible measurement sequence in step S1 or during a former implementation of step S4), the bright images already formerly detected for the gain level can be used anew. To put it another way, during the current implementation of the measurement sequence, it is possible to dispense with detecting once again the bright images already formerly detected. Instead, the bright images of the corresponding gain levels can be used anew in the context of the current measurement sequence and can be read out from a memory, for example. In this case, how many formerly detected bright images are taken into account may depend on the repetition parameter of the current parameter set. This variant, too, helps to reduce the method duration.

Furthermore, provision can be made, in the context of the method, for implementing at least one measurement sequence for which only one gain level is used (i.e., for which the gain parameter is set to 1). In this case, however, the repetition parameter is typically set to a value of more than 1, for example to 5 or 10. This procedure can make it possible to deduce whether the detector 22 has a linear sensitivity curve, for example if the resulting quality value is comparatively high.

Additionally or alternatively, provision can be made, in the context of the method, for implementing at least one measurement sequence for which more than one gain level is provided. This can make it possible to deduce whether the detector 22 has a nonlinear sensitivity curve, for example if the resulting quality value is comparatively high.

Figure 2:
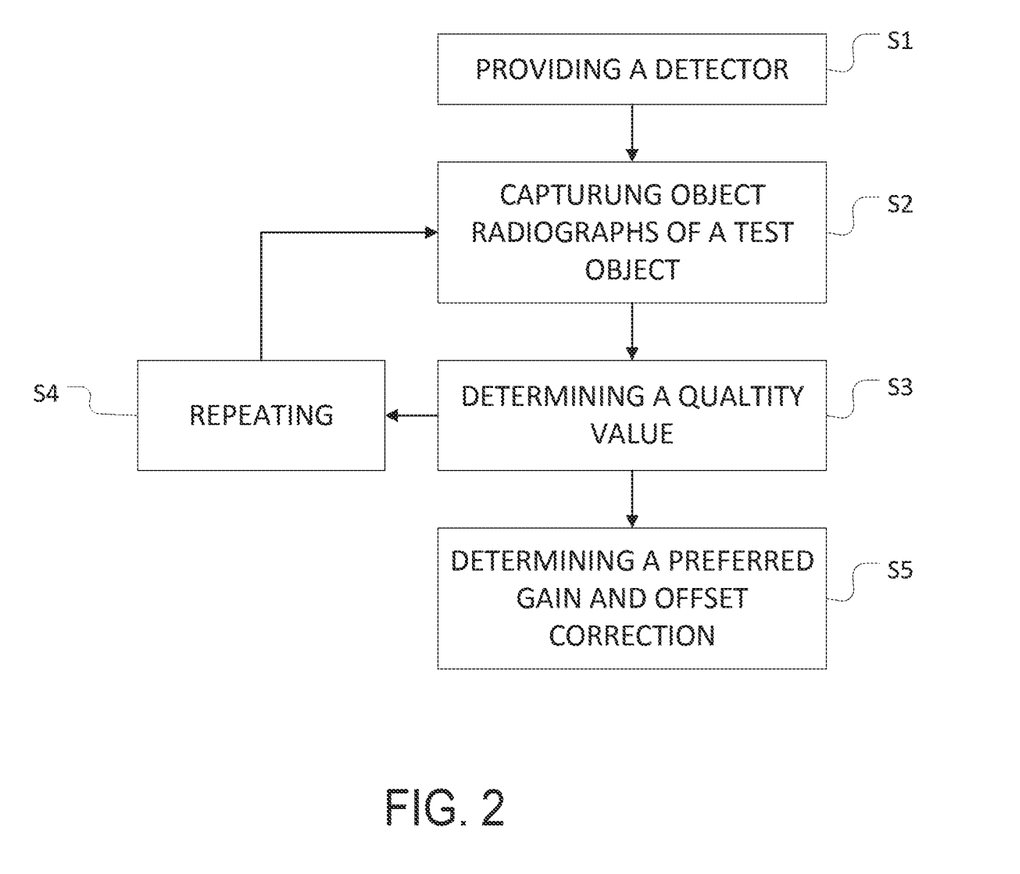
FIG. 2 illustrates a flowchart of a method according to an exemplary embodiment of the invention.

The process of determining the quality value in accordance with step S3 from FIG. 2 is explained in greater detail below with reference to the sectional illustrations in FIGS. 3A and 3B and also 4A and 4B. FIG. 3C shows the test object 24 in a three-dimensional representation. It is evident that the test object 24 is configured as an elongate cylinder having a circular cross section. In particular, the test object 24 can be configured as a solid aluminum cylinder having a circular cross section and can have a substantially homogeneous density distribution. If the test object 24 is measured and reconstructed by the CT scanner, the center axis M of the test object 24 can coincide with the axis of rotation R from FIG. 1. However, FIGS. 3A and 3B and also 4A and 4B illustrate a situation in which the center axis M and the axis of rotation R do not coincide.

Figure 3A:
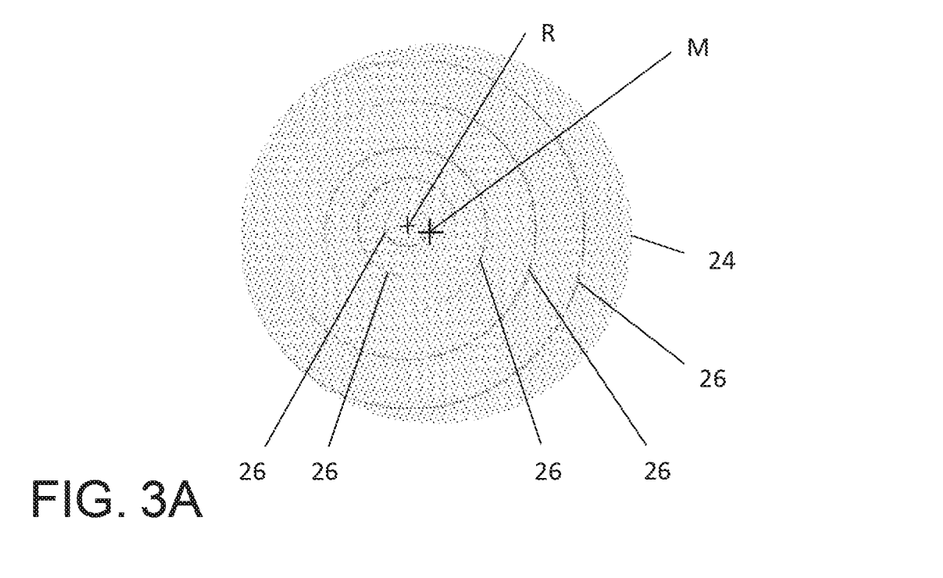
FIG. 3A illustrates a horizontal section through a first reconstructed three-dimensional representation of a test object.

FIG. 3A shows a horizontal cross section through a reconstructed representation of the test object 24 (i.e., a sectional view in a plane perpendicular to the center axis M). On account of the cylinder shape of the test object 24, the cross section is circular. Firstly, a substantially uniform grayscale distribution in the reconstructed image is clearly discernible. It is additionally discernible that a plurality of ring-shaped image disturbances extend around the axis of rotation R. The image disturbances are the ring artefacts 26 mentioned above. In practice, unlike in the schematic illustration, the circular lines are not lines of uniform width, nor are they regularly interrupted lines. Nevertheless, in practice, circular, line-like structures having interruptions are clearly discernible in the image, which are composed, e.g., of image points having darker grayscale values than in the vicinity of the line-like structure. The ring artefacts 26 represent quality deficiencies of a reconstructed image, which hamper for example a more accurate examination or automatic evaluation of the reconstructed three-dimensional representation.

The terms "near the center" and "remote from the center" or "outward" as a description of opposites relate to the axis of rotation R.

Figure 3B:
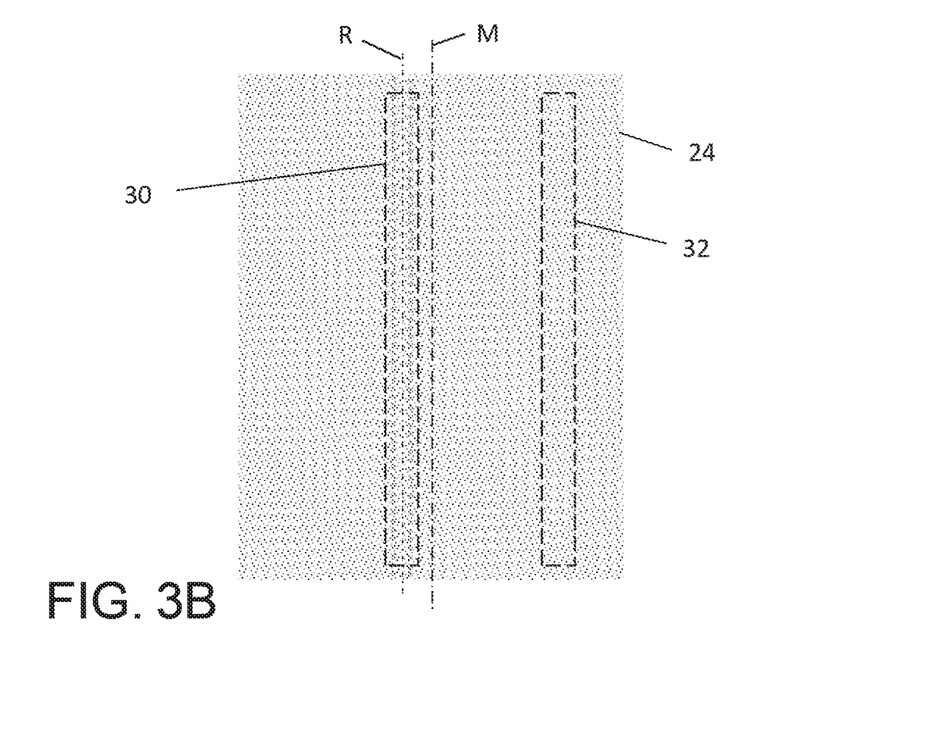
FIG. 3B illustrates a vertical section through the first reconstructed three-dimensional representation of a test object in accordance with FIG. 3A, wherein the process of determining a quality value for the reconstructed three-dimensional representation is indicated schematically.
Figure 3C:
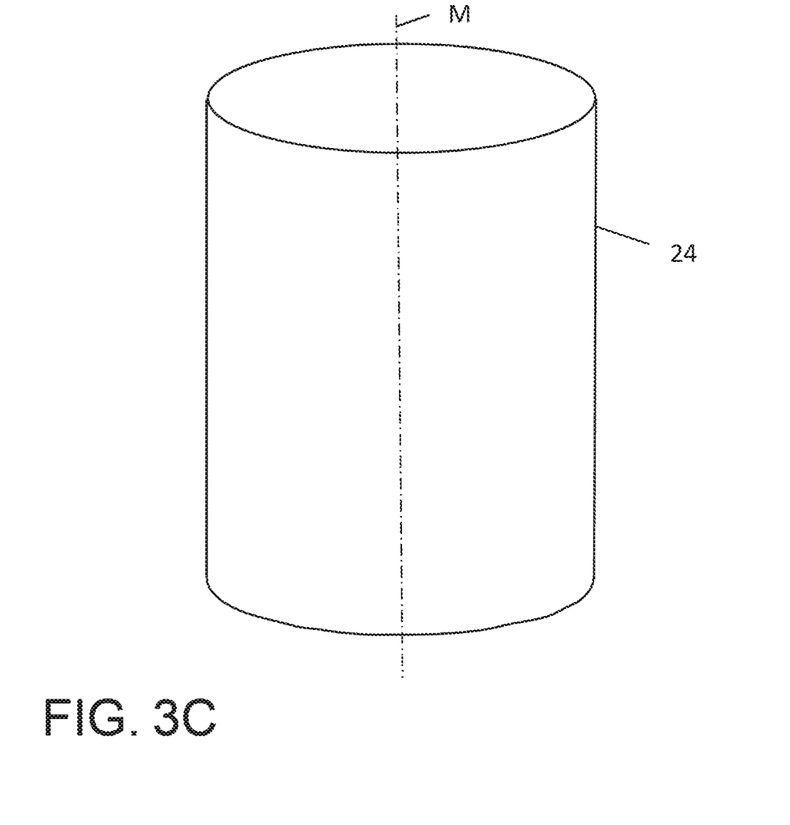
FIG. 3C illustrates a three-dimensional representation of a test object which is reconstructed three-dimensionally by a CT scanner.

FIG. 3B shows a reconstructed representation of a vertical cross section through the center axis M of the test object 24. On account of the cylinder shape of the test object 24, the cross section is rectangular. A substantially uniform grayscale distribution in the reconstructed image is clearly discernible. By contrast, a distinct variation of grayscale values in the image is visible in a region to the left of the center axis M. The axis of rotation R is arranged in the region.

Ring-shaped structures of the ring artefacts 26 primarily in the region near the center are discernible only in the cross-sectional view in accordance with FIG. 3A, but not in the vertical section in accordance with FIG. 3B.

The insight that the ring artefacts 26 are located primarily in the region near the center is exploited by the method for determining the quality value according to an exemplary embodiment of the invention. As is shown in FIG. 3B, for this purpose two image regions of the reconstructed three-dimensional representation of the test object 24 in the form of a first region 30 and a second region 32 are selected, and the signal-to-noise ratio is determined for each region 30, 32. In this case, the first region 30 is arranged near the center, and the second region 32 remote from the center. In this case, in particular those pixels and/or image regions which have a grayscale value that deviates unusually from adjacent pixels and/or adjacent image regions are combined as noise component. By way of example, it is possible to form a difference between the grayscale value of a pixel and the grayscale values of adjacent pixels. If the difference exceeds a threshold value, the corresponding pixel can be assigned to the noise component. By contrast, if the threshold value is not exceeded, no unusual deviation is present and the corresponding pixel can be assigned to the signal or used component. By forming the quotient of signal component to noise component, it is then possible to determine the signal-to-noise ratio, which in the case of high image qualities assumes a correspondingly high value.

Alternatively or additionally, the number and/or density of the circle artefacts 26 can be determined for example from the cross section illustrated in FIG. 3A. In particular a higher number and thus a greater density of the circle artefacts 26 can also be observed in the region near the center if the quality of the reconstruction is low. In a similar manner to that as described above, it is therefore also possible to compare the difference in the density of the circle artefacts (i.e., the difference in the distances between the discernible annula) in the region near the center and in a region lying radially further outward. This difference, in particular, can be determined as a measure of the quality. As already indicated, another measure of the quality is the number of circle artefacts in the entire horizontal cross section. The terms horizontal cross section and vertical cross section do not restrict the invention to the axis of rotation extending from bottom to top, even if this is often the case in practice. The horizontal section or horizontal cross section extends in a plane transversely and in particular perpendicularly to the axis of rotation. The vertical cross section extends in a plane extending transversely or perpendicular to the plane of the horizontal cross section and contains in particular a portion of the axis of rotation.

In the case of FIG. 3B, the first region 30 near the center has a recognizably higher noise component than the second region 32 remote from the center. Accordingly, the signal-to-noise ratio is lower for the first region 30 near the center than for the second region 32 remote from the center. The quality value for the reconstructed three-dimensional representation can again be determined by forming a difference between the two signal-to-noise ratios or a quotient thereof. The inventor has recognized that, the smaller the difference or the closer the quotient is to a value of 1, the smaller the extent of the ring artefacts 26 in the reconstructed three-dimensional representation. In other words, the difference and/or the quotient thus form(s) a value to quantify the extent of the ring artefacts 26 in the reconstructed three-dimensional representation. However, the quality of the reconstruction can also be established independently of whether ring artefacts 26 are able to be ascertained in the cross section, on the basis of the difference in the signal-to-noise ratio in the region near the center and in an outer region.

In principle, the invention can also provide for selecting only one of the regions 30, 32 for determining the quality value, and using in particular the first region 30 near the center and the signal-to-noise ratio there as a quality value. Alternatively, as a quality value, it is possible to determine the number and/or the averaged distance between the ring artefacts 26 in the cross-sectional views from FIG. 3A and from FIG. 3B.

Figure 4A:
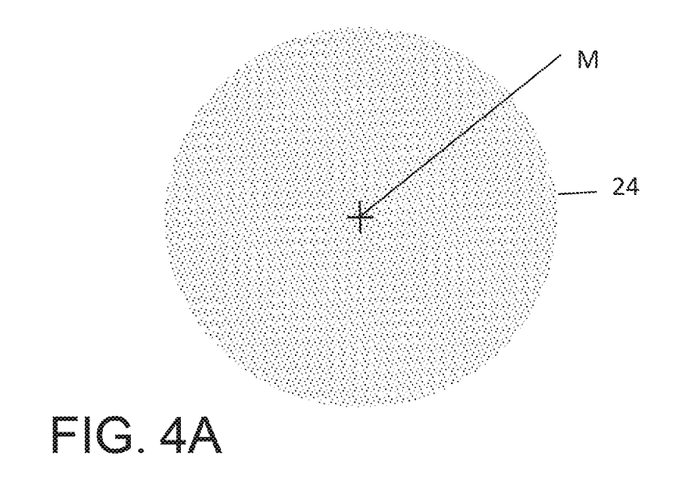
FIG. 4A illustrates a horizontal section through a second reconstructed three-dimensional representation of a test object.
Figure 4B:
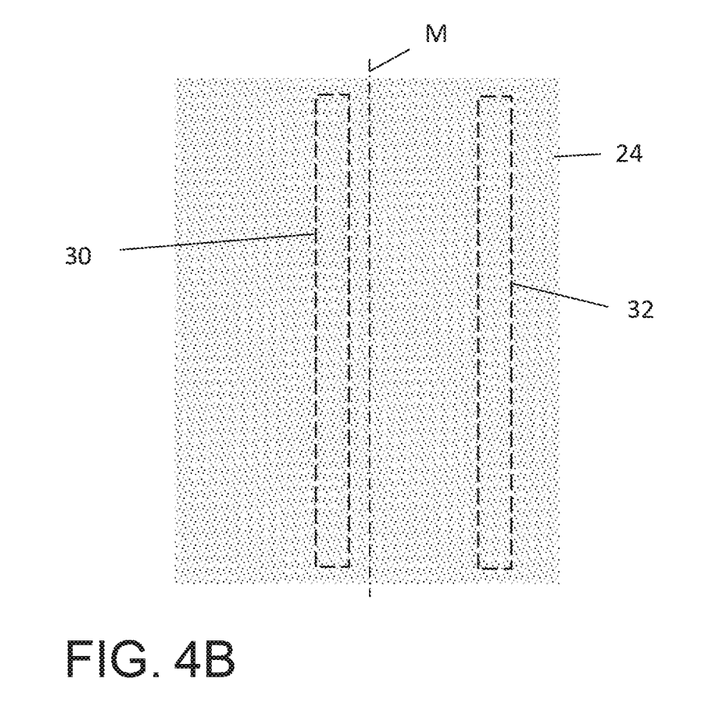
FIG. 4B illustrates a vertical section through the second reconstructed three-dimensional representation of an test object in accordance with FIG. 4A, wherein, in a manner similar to that in FIG. 3B, the process of determining a quality value for the reconstructed three-dimensional representation is indicated schematically.

FIGS. 4A and 4B show sectional illustrations corresponding to FIGS. 3A and 3B, but for a three-dimensional reconstruction of the test object 24 with higher quality than in the case of FIGS. 3A and 3B.

Ring artefacts are no longer discernible in the case of FIG. 4A. Moreover, the mean grayscale value is of identical magnitude in the region near the center and in the outer region of the cross section.

Figure 5:
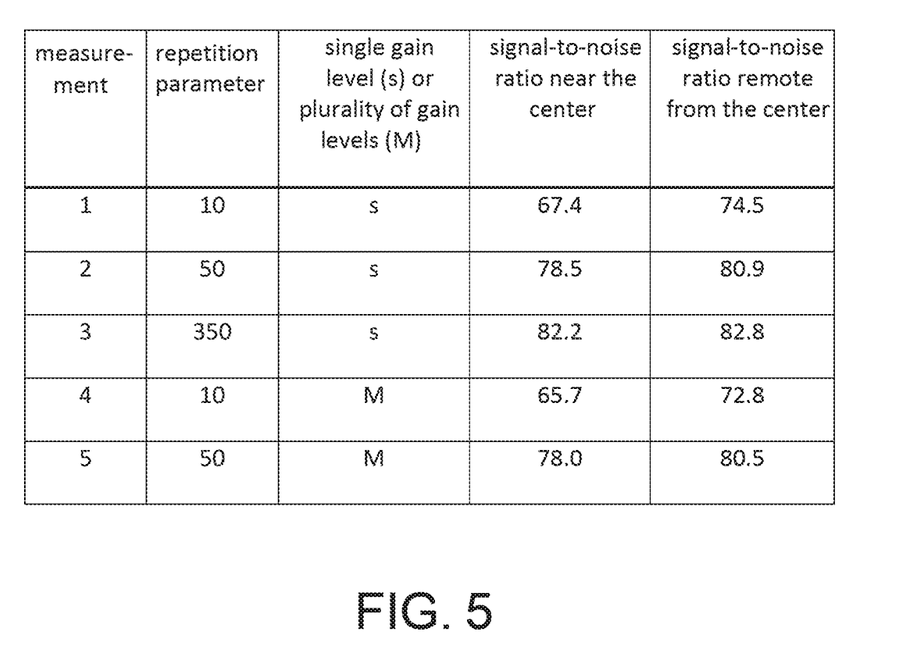
FIG. 5 illustrates a comparison of the quality values finally obtained for different setting values of the gain and offset correction.

The measurement results for one example of the method according to an exemplary embodiment of the invention are summarized in tabular form in FIG. 5. These measurement results are present after passing through steps S2 and S3 five times, with a repetition of these steps likewise involving passing through step S4 in each case (a total of four times). To put it more precisely, the first measurement (or the first pass) in accordance with FIG. 5 is obtained by implementing steps S1-S3 and the second to fifth measurements (or passes) are obtained in each case by implementing steps S4, S2 and S3. For determining a suitable or optimum gain and offset correction, the measurement results summarized in FIG. 5 are analyzed more closely in step S5 in accordance with FIG. 2.

In detail, FIG. 5 shows for each pass the most important parameters taken as a basis for carrying out the measurement sequences for a respectively associated gain and offset correction. In particular, the repetition parameter per gain level is indicated, as is the fact of whether just one or a plurality of the gain levels were considered (that is to say whether the gain parameter has a value of 1 or a larger value). Furthermore, the signal-to-noise ratio near the center in the first region 30 in accordance with FIG. 4 and the signal-to-noise ratio remote from the center in the second region 32 in accordance with FIG. 4 are indicated for each pass. It is evident that the signal-to-noise ratio near the center actually always has a lower value than the signal-to-noise ratio remote from the center. Furthermore, it is evident that different signal-to-noise ratios arise for the individual passes depending on the parameters taken as a basis for the measurement sequence (and thus depending on the resultant setting values for the gain and offset correction).

Overall, the best quality value arises for pass 3, since here a difference between the relevant signal-to-noise ratios reaches merely an absolute value amounting to 0.6 and the quotient of the signal-to-noise ratios is almost 1.

The setting values for the gain and offset correction that are taken as a basis for this pass were determined by a measurement sequence for which only one gain level was considered. However, three hundred and fifty bright image captures and thus an extremely comprehensive averaging were performed for the gain level. It is noticeable that, for example, pass 5 with a plurality of gain levels and still fifty bright image captures per gain level does not yield a better result. This indicates that the detector 22 in the example shown is extremely likely to have a linear sensitivity curve. In the case of such a linear detector 22, measurement with a plurality of gain levels may entail the undesired generation of outliers, which can result in a less suitable gain and offset correction and thus a less precise three-dimensional reconstruction of the test object 24.

Overall, in the case of the example shown, therefore, implementing just five object radiography and 3D reconstruction processes with respectively different setting values for the gain and offset correction of the detector 22 resulted in determining, in a time-saving manner and with little complexity, which gain and offset correction (or which parameters for implementing a measurement sequence for determining the setting values for the gain and offset correction) yields the most precise results and enables the most precise 3D reconstruction. A subsequent actual workpiece checking can then be implemented on the basis of this best suitable or optimum gain and offset correction. The measurement sequence with the parameters concerning pass 3 can once again be implemented for this purpose. Alternatively, the setting values already formerly determined for the pass 3 can be read out from a memory.

It is understood that the foregoing description is that of the exemplary embodiments of the invention and that various changes and modifications may be made thereto without departing from the spirit and scope of the invention as defined in the appended claims.

What is claimed is:

1. A method for correcting a detector configured to generate object radiographs, the method comprising the steps of:
   (a) providing the detector having setting values for a gain and offset correction;
   (b) capturing a plurality of object radiographs of a test object by the detector and generating a reconstructed three-dimensional representation of the test object based on the plurality of object radiographs;
   (c) determining at least one quality value of the reconstructed three-dimensional representation;
   (d) repeating steps (b) and (c) at least once subsequent to generating a parameter set, executing a measurement sequence based on the parameter set, and determining at least one setting value for the gain and offset correction of the detector anew based on the measurement sequence; and
   (e) determining a preferred gain and offset correction of the detector based on a plurality of quality values determined overall.

2. The method as claimed in claim 1, wherein the parameter set includes at least one of the following parameters:
   a dark image parameter defining a number of dark images to be captured;
   a gain parameter defining a number of gain levels for capturing bright images; and
   at least one repetition parameter defining at least one of a number of bright image detections per gain level or an individual gain level.

3. The method as claimed in claim 1, wherein the gain and offset correction in step (a) is carried out based on initial setting values.

4. The method as claimed in claim 1, wherein:
   the gain and offset correction in step (a) is carried out based on initially carrying out the measurement sequence for determining the setting values for the gain and offset correction, and
   the parameter set in step (d) is chosen to permit a deviating measurement sequence to be carried out which deviates from the measurement sequence carried out in step (a).

5. The method as claimed in claim 1, further comprising:
   a plurality of repetitions in accordance with step (d),
   wherein before a respective repetition, the parameter set is generated to permit a deviating measurement sequence to be carried out which deviates from measurement sequences carried out during already carried out repetitions.

6. The method as claimed in claim 1, wherein a former number of dark images detected for a former gain and offset correction of the detector is also at least partly taken as a basis for a repeated gain and offset correction in accordance with step (d).

7. The method as claimed in claim 1, wherein when a repetition in accordance with step (d) involves once again passing through a formerly already detected gain level, the bright images formerly detected for this gain level are at least partly taken as a basis for the gain and offset correction in step (d).

8. The method as claimed in claim 1, wherein the at least one quality value indicates an extent of ring artefacts in the reconstructed three-dimensional representation.

9. The method as claimed in claim 1, wherein:
   the at least one quality value is determined based on a signal-to-noise ratio in the reconstructed three-dimensional representation, and
   the signal-to-noise ratio is determined for different regions of the reconstructed three-dimensional representation.

10. The method as claimed in claim 1, wherein:
    the at least one quality value is determined based on a signal-to-noise ratio in the reconstructed three-dimensional representation, and
    the signal-to-noise ratio is determined for a first region, which images a region of the test object that is near a center, and for a second region, which images a region of the test object that is remote from the center.

11. The method as claimed in claim 1, wherein at least one measurement sequence with only one gain level and/or at least one measurement sequence with more than one gain level are/is carried out.

12. An object radiography arrangement comprising:
    the detector configured to generate object radiographs;
    a radiation source configured to direct invasive electromagnetic radiation onto the detector;
    an evaluation unit configured to determine the at least one quality value of the reconstructed three-dimensional representation generated based on the object radiographs; and
    a control device configured to control the arrangement to implement the method as claimed in claim 1.

* * * * *